(12) United States Patent
Tsuda et al.

(10) Patent No.: US 6,346,172 B1
(45) Date of Patent: Feb. 12, 2002

(54) PROCESS FOR PRODUCING DIFLUOROMETHANE

(75) Inventors: Takehide Tsuda; Takashi Shibanuma, both of Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/242,692

(22) PCT Filed: Aug. 26, 1997

(86) PCT No.: PCT/JP97/02963

§ 371 Date: Apr. 13, 1999

§ 102(e) Date: Apr. 13, 1999

(87) PCT Pub. No.: WO98/08790

PCT Pub. Date: Mar. 5, 1998

(30) Foreign Application Priority Data

Aug. 27, 1996 (JP) ............................................. 8-224846

(51) Int. Cl.⁷ ....................... C07C 17/383; C07C 51/44; B01D 3/00
(52) U.S. Cl. .............................. 203/14; 203/91; 570/178
(58) Field of Search ................................. 570/167, 177, 570/178; 203/14, 91, 100

(56) References Cited

U.S. PATENT DOCUMENTS

| | | | | |
|---|---|---|---|---|
| 5,344,998 A | * | 9/1994 | Martin et al. ............... | 568/683 |
| 5,495,057 A | * | 2/1996 | Nam et al. .................... | 570/167 |
| 5,523,015 A | * | 6/1996 | Tsuda et al. .................. | 203/50 |
| 5,785,822 A | * | 7/1998 | Cerri et al. .................... | 203/67 |
| 5,800,682 A | * | 9/1998 | Cerri et al. .................. | 570/178 |

FOREIGN PATENT DOCUMENTS

| | | |
|---|---|---|
| EP | 0128510 A2 | 12/1984 |
| GB | 707145 A | 4/1954 |
| JP | B 42-3004 | 2/1967 |
| JP | 59231030 A | 12/1984 |
| JP | A 59-2312030 | 12/1984 |
| JP | 6327968 A | 11/1994 |
| JP | 733695 A | 2/1995 |
| JP | 7305054 A | 11/1995 |
| JP | A 8-143487 | 6/1996 |
| JP | 8173799 A | 7/1996 |
| JP | A 8-183748 | 7/1996 |

* cited by examiner

Primary Examiner—Virginia Manoharan
(74) Attorney, Agent, or Firm—Birch, Stewart, Kolasch & Birch, LLP

(57) ABSTRACT

A process for refining difluoromethane by removing water which is contained in difluoromethane and has been believed to be difficult to be removed includes distilling difluoromethane which contains water so as to obtain difluoromethane as a distillate and a mixture as a bottom product of difluoromethane and chlorofluoromethane and/or dichloromethane which mixture contains water. The bottom product is recycled to a reaction step to be reused together with a feedstock.

8 Claims, 1 Drawing Sheet

PROCESS FOR PRODUCING DIFLUOROMETHANE

This application is the national phase under 35 U.S.C. §371 of prior PCT International Application No. PCT/JP97/02963 which has an International filing date of Aug. 26, 1997 which designated the United States of America.

TECHNICAL FIELD

The present invention relates to a process for producing difluoromethane (hereinafter, also referred to as "HFC-32") having a high purity by removing water by means of distillation from a mixture of HFC-32 comprising water, for example a reaction product comprising HFC-32 and water which product is prepared by a production process for HFC-32 by means of fluorination of dichloromethane (hereinafter, also referred to as "HCC-30").

BACKGROUND ART

Recently, the ozone layer depletion of the stratosphere by means of chlorofluorocarbons has been a serious problem, and the uses thereof are prohibited internationally. Further, productions and uses of hydrochlorofluorocarbons are also restricted. HFC-32 as a compound free from chlorine has an ozone sphere destruction factor of zero and thus its global warming factor is small, and has a good freezing capacity, so that HFC-32 is said to be favorable as an alternative cooling medium in place of the chlorofluorocarbons which are restricted.

As a production process of HFC-32, there are, for example, a process in which HCC-30 is fluorinated, and a process in which dichloromethane or/and chlorodifluoromethane are reduced. In these production processes, water (or moisture) is contained in HFC-32 as an aimed product because of water contained in a feedstock and water entrained with a catalyst, as well as water or an alkaline aqueous solution used for removal of unreacted hydrogen fluoride and hydrogen chloride as a by-product.

Generally, a solid dehydration agent such as a zeolite is often used for the removal of water contained a halogenated hydrocarbon. For example, Japanese Patent Kokai Publication No. 7-33695 discloses the use of a dehydrated zeolite for the removal of water in 1,1-dichloro-1-fluoroethane (hereinafter, also referred to as "HFC-141b") and further discloses that HFC-141b is not decomposed by the dehydration agent. When such a solid dehydration agent is used, it is required to have a step and an apparatus to regenerate the dehydration agent. In addition, there occurs a loss of an aimed product which has been adsorbed onto the solid dehydration agent upon the regeneration of the agent.

As to HFC-32, it is required to have a particularly less water content and thus a high purity since it is mostly used as a cooling medium, so that a large amount of a solid dehydration agent is necessary. On the other hand, since a molecular size of HFC-32 is close to that of water, a dehydration ability of the usual solid dehydration agent such as a zeolite is not sufficient, and in addition, HFC-32 is decomposed. Therefore, there is a problem in that that it is difficult to dehydrate HFC-32 compared with the other usual halogenated hydrocarbon.

Thus, the water removal from HFC-32 requires a specific solid dehydration agent, and water removal processes using such solid dehydration agents are proposed in Japanese Patent Kokai Publication Nos. 6-327,968, 7-305,054 and 8-173,799. Those solid dehydration agents are useful when they are used in a closed system as used in a compressor as a cooling medium for an air conditioner (that is, when no water gets into the system from the outside thereof)(See Japanese Patent Kokai Publication No. 7-305,054). However, when water is continuously supplied into a system through a feedstock and so on as in a production step of HFC-32, a dehydration agent is required which has a high performance (a high water adsorption capacity, a high water selectivity on adsorption). When the dehydration agent is regenerated, HFC-32 which has been adsorbed onto the dehydration agent is finally wasted, and therefore, a large amount of HFC-32 is lost if the performance is bad.

In the case in which water is continuously supplied into a system from the outside thereof, water may be removed by reaction of water with lithium chloride. However, this way is only able to lower a water content in HFC-32 to substantially about 500 ppm. Even in this way, lithium chloride has to be regenerated.

DISCLOSURE OF THE INVENTION

It is an object of the present invention to provide a process for producing HFC-32 of which water content is small wherein the water removal from HFC-32 which has been said to be difficult as described above is carried out effectively by means of an easy operation, and in other words to provide a process for refining HFC-32.

When an impurity is separated from the other using a distillation operation, as to an ideal mixture, it is generally said that a boiling point difference between components which constitute the mixture is a measure for an ease extent of the separation. However, a mixture which contains water is largely non-ideal, and separation behaviors of such a mixture are complicated. Thus, as to the water separation, a relative volatility or a vapor-liquid ratio, namely a water content in a vapor phase/a water content in a liquid phase (based on molar concentration) of a system in question becomes important.

For example, a boiling point of trichlorofluoromethane (hereinafter, also referred to as "CFC-11") is about 24° C. at atmospheric pressure, which is far lower than 100° C. which is a boiling point of water, so that it is expected that a relative volatility of water is considerably smaller than one in a CFC-11/water system. However, when the relative volatility is actually measured, the measurement shows, inversely to the expectation, that the relative volatility is larger than one, that is the water content in the vapor phase is larger than that of the liquid phase.

Such an inversion phenomenon is also observed with respect to dichlorodifluoromethane of which boiling point is further lower (about −30° C., and hereinafter, also referred to as "CFC-12"). On the other hand, with respect to chlorofluoromethane of which boiling point (about −9° C., and hereinafter, also referred to as "HCFC-31") is between those of CFC-11 and CFC-12, the relative volatility of water is contrary smaller than one. In addition, even when it is expected in accordance with a difference between boiling points whether the relative volatility of water is larger or smaller than one, there is still a problem in that a figure of the relative volatility itself cannot be expected at all.

For example, in the case of HCFC-31 with which the relative volatility of water is smaller than one, if the system of water-HCFC-31 were ideal, the relative volatility of water is expected to be 0.0073 at a temperature of 25° C. by means of calculation in accordance with Raoult's law. This figure means that it is extremely easy to separate water from HCFC-31 by distillation. However, when the relative volatility of water is measured in such a system, it measured to be about 0.79, which is about one hundred times as large as that of the above expectation, and it is found for the first time that the separation between water and HCFC-31 is no so easy.

What is described above means that how much the relative volatility is larger or smaller than one is unknown based on the difference between boiling points before it is actually measured. When a figure of the relative volatility is unknown, no number of theoretical plates required for the distillation cannot be determined for the separation in the industrial scale. Therefore, it is unknown how many numbers of the theoretical plates in a distillation column is to be used in order to separate water from HFC-32. That is, there occurs a problem in that whether or not water is industrially separated from HFC-32 is unknown.

As described above, when water is contained as a component which constitutes a system, it is not expected at all differently from the usual distillation operation whether a relative volatility of water is larger or smaller than one is determined only based on a boiling point difference, and further how much a figure of the relative volatility is, so that it is also not easy at all to expect water behaviors (for example, whether being concentrated in an enriching section or a stripping section by means of the distillation, the number of necessary plates for the distillation and so on).

Then, the present inventors have measured relative volatilities of water in a water/HFC-32 system, a water/HCFC-31 system and a water/HCC-31 system, intensively studied the results of the measurement as to whether water content in HFC-32 can be separated by the distillation, and found that such separation is possible, so that the present invention has been completed.

For example, the relative volatility of water was measured to be 0.20 at a temperature of 25° C. and a pressure of 17 kg/cm$^2$-abs. (absolute pressure) in the water/HFC-32 system. By thus actually measuring the relative volatility of water, it has been expected for the first time that water contained in HFC-32 can be removed while concentrating water in the stripping section by means of the distillation, which has been confirmed.

Therefore, the present invention provides a process for producing a mixture comprising water and HFC-32 in which mixture a water content has been substantially reduced, and preferably for producing a mixture comprising HFC-32 which contains substantially no water characterized in that a mixture comprising water and HFC-32 is subjected to a distillation operation.

In one embodiment of the present invention, the mixture which is subjected to the distillation operation consists substantially of water and HFC-32, and the mixture after the distillation operation consists substantially of HFC-32 of which water content has been reduced and preferably HFC-32 which contains substantially no water.

Figure 1:
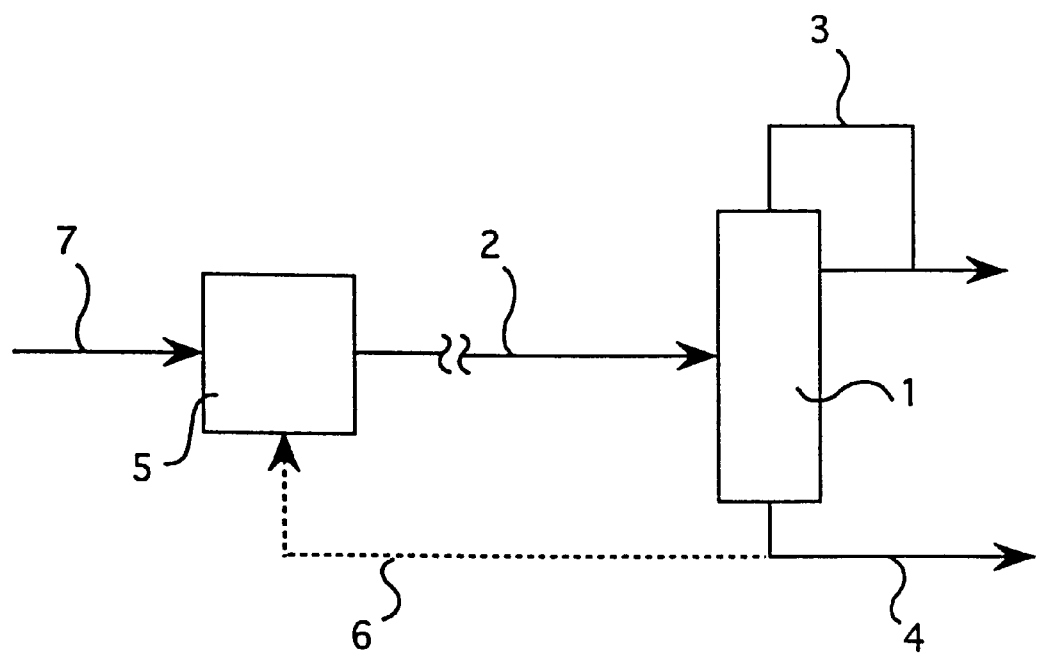
FIG. 1 schematically shows one preferable embodiment of the present invention by means of a flow sheet.

In the drawing, reference numbers show the following:
1. distillation process
2. feedstock to distillation process
3. distillate
4. bottom product
5. reaction step
6. recycling stream
7. feedstock to reaction step

DETAILED DESCRIPTION OF THE INVENTION

In the present invention, "a water content has been substantially reduced" means that an amount of water in the mixture after the distillation is smaller than that prior to the distillation (for example, being reduced to 50%, and preferably to 5% of the originally contained water), and generally equivalent to that a water concentration of the mixture is reduced.

In a preferable embodiment, the distillation operation of the present invention is carried out at an operation pressure (for example, an operation pressure at the top of a distillation column) in the range of 10 to 40 kg/cm$^2$-abs., preferably in the range of 15 to 35 kg/cm$^2$-abs. and more preferably in the range of 20 to 30 kg/cm$^2$-abs, and in such an operation, a distillate temperature (for example, a temperature at the top of the distillation column) is in the range of 5 to 60° C., in the range of 20 to 55° C., and in the range of 30 to 50° C. respectively when HFC-32 is distilled off which contains substantially no water. Usually, a temperature of a reflux stream which is returned to the top of the distillation column after the distillation and condensation is preferably the same as that of the distillate. As clearly seen from Example 2 which will be described later, by subjecting HFC-32 containing water at 200 ppm by weight to the distillation operation at a pressure of 20 kg/cm$^2$-abs., HFC-32 was obtained which contained water only at not larger than 10 ppm by) weight.

During further studies, relative volatilities of water in the water/HCFC-31 system and the water/HCC-30 system have been measured to be 0.79 and 7.94 respectively. Considering these measurements and the relative volatility of water in the water/HFC-32 system described above as well as boiling points of HFC-32, HCFC-31 and HCC-30 being −52° C., −9° C. and 40° C. respectively, it is expected for the first time that even when a mixture of these three components and water is subjected to a distillation operation, water is concentrated between HCFC-31 and HCC-30 so that water is substantially separated from HFC-32. As clearly seen from Example 3, which will be described later, by subjecting a mixture of HFC-32, HCFC-31 and HCC-30 which mixture contained water at 400 ppm by weight to the distillation at a pressure of 20 kg/cm$^2$-abs., HFC-32 was obtained which contained water only at not larger than 10 ppm by weight.

The process of the present invention is preferably applied to a case wherein HFC-32 (or a mixture of HFC-32 with HCFC-31 and/or HCC-30) contains water at an saturated amount or less (usually, the water concentration being about 500 ppm by weight or less, and preferably 100 ppm by weight or less), and when water is contained excessively above the saturation, it is generally preferable to carry out phase separation into two liquid phases so as to obtain an HFC-32 phase, only to which the present process is applied. When the water-containing mixture to be subjected to the distillation contains in addition to HFC-32, HCFC-31 and/or HCC-30, amounts of HCFC-31 and/or HCC-30 are not particularly limited. Usually, a concentration of HFC-32 in the mixture is in the range of about 30 to 100% by weight (100% means that the mixture contains water in an order of several hundreds or several tens of ppm), preferably in the range of about 50 to 100% by weight, and more preferably in the range of about 70 to 100% by weight.

When the water-containing mixture to be subjected to the distillation contains in addition to HFC-32, HCFC-31 and/or HCC-30 as the other component(s), an operation pressure of the distillation of the present invention is in the range of 10 to 40 kg/cm²-abs., preferably in the range of 15 to 35 kg/cm²-abs. and more preferably in the range of 20 to 30 kg/cm²-abs, and in such an operation pressure, a temperature at the top of the distillation column is in the range of 5 to 60° C., in the range of 20 to 55° C., and in the range of 30 to 560° C. respectively, which is particularly advantageous from viewpoints of costs for pressure resistant apparatus and utilities. It is noted that even when those other components are present, HFC-32 of which water content is reduced from the top of the distillation step is obtained.

Concrete Embodiments to Carry Out the Invention

Next, the present invention will be explained concretely with reference to the accompanied drawing. FIG. 1 schematically shows one preferable embodiment of the present invention by means of a flow sheet.

In FIG. 1, the water-containing mixture 2 which contains HFC-32 as a main component is continuously supplied to the distillation column 1. In the distillation operation, HFC-32 having a high purity (namely, substantially no water being contained) is distilled off at the top of the column as the distillate 3, and a mixture which contains water and the balancing HFC-32 is obtained as the bottom product 4. When the mixture 2 contains in addition to HFC-32, HCFC-31 and HCC-30, these additional components are also withdrawn together as the bottom product, which is seen from the relative volatilities described above.

The withdrawn bottom product 4 is effectively used by recycling it to the reaction step 5 which produces HFC-32 when the product 4 contains HCFC-31 and/or HCC-30 so that they are effectively processed together with the feed-stock 7 (as shown with the broken line 6 in FIG. 1). Further, when the bottom product 4 consists substantially of HFC-32 and water, it may be recycled to a step in which hydrogen chloride or hydrogen fluoride is removed, for example a water washing tower or an alkali washing tower.

Since in a practical distillation, the number of plates cannot be increased ideally, the mixture comprising HFC-32 and water is separated into HFC-32 which contains substantially no water or which contains almost no water as well as balancing HFC-32 which contains concentrated water. The HFC-32 which contains such concentrated water may be withdrawn outside from a system and water may be disposed of. Rather, it is preferable to treat in some manner (for example, an adsorption treatment by means of a solid dehydration agent) so as to remove water and to recover HFC-32. In the latter case, water in the HFC-32 is desirably concentrated as much as possible (namely, a concentration of HFC-32 is lowered.) However, in a more preferable embodiment, such water-containing HFC-32 is not withdrawn outside the system but processed within the system. For example, it is desirable that the bottom product containing HFC-32 in which water is concentrated is recycled to the reaction step 5 so that water is not withdrawn outside the system.

When the bottom product 4 is recycled as described above, it is advantageous to use an antimony catalyst (for example a halogenated antimony) in the reaction step 5 for the production of HFC-32 by means of fluorination of HCC-30. This is because the water contained in the bottom product 4 is absorbed by the antimony catalyst so that water is removed when the bottom product 4 is recycled to the reaction step. When degraded catalyst is regenerated, only the absorbed water is simultaneously reacted and removed outside the system and HFC-32 is left as it is within the system. When water-containing HFC-32 which has been separated by the distillation is processed alone, some loss of HFC-32 occurs even though water is concentrated in HFC-32. To the contrary, almost no loss of HFC-32 advantageously occurs in the combination of the antimony catalyst with HFC-32 which contains water.

It is noted that the process according to the present invention can be carried out using a conventional distillation apparatus continuously or batchwise.

INDUSTRIAL APPLICABILITY

The process for the production of difluoromethane according to the present invention subjects the mixture of difluoromethane as well as chlorofluoromethane and/or difluoromethane which mixture contains water to the distillation so that water which has been difficult to be removed is easily removed from difluoromethane, whereby difluoromethane can be obtained at its higher concentration.

EXAMPLES

Next, the present invention will be explained in detail with reference to Examples.

Example 1

Charged in a stainless vessel was CFC-13, HFC-32, CFC-12, HCFC-31, CFC-11, HCC-30 or CFC-113 (1,1,2-trichloro-1,2,2-trifluoroethane) each containing a saturated amount of water, and a relative volatility (based on mole) of water was measured at a predetermined temperature. The results are shown in Table 1.

TABLE 1

| Compound | Relative Volatility | | |
|---|---|---|---|
| (Normal Boiling Point) | 0° C. | 25° C. | 50° C. |
| CFC-13 (−81° C.) | 2.00 | 1.00 | 1.00 |
| HFC-32 (−52° C.) | 0.22 | 0.20 | 0.16 |
| CFC-12 (−30° C.) | 10 | 7 | 5 |
| HCFC-31 (−9° C.) | 1.00 | 0.79 | 0.50 |
| CFC-11 (24° C.) | 70 | 40 | 20 |
| HCC-30 (40° C.) | 8.91 | 7.94 | 6.31 |
| CFC-113 (47° C.) | 100 | 70 | 40 |

According to the results of Table 1, the following is seen: it is presumed that all the system are those in which water is easily concentrated in the liquid phase (relative volatility<1), but since their behaviors are unequal, their relative volatilities are unknown prior to the measurement thereof. That is, based on the measurement results, it is seen that the relative volatility of water in the water/HFC-32, HCFC-31 or HCC-30 system is necessary and sufficient for the separation of one from the other using the distillation when an operation temperature is appropriately selected, so that the separation of water from HFC-32 (and HCFC-31 and/or HCC-30) through the distillation is possible. That is, as to HFC-32 and HCFC-31, the relative volatility is smaller than one so that water is concentrated in the liquid phase, and as to HCC-30, the relative volatility is larger than one so that water is concentrated in the vapor phase.

Example 2

300 kg of HFC-32 which contained water at 200 ppm by weight was supplied into a stainless steel distillation column having a diameter of 150 mm and 24 theoretical plates. Carrying out batchwise distillation at a pressure of the column top of 20 kg/cm²-abs. (a top temperature was 30°

C.), the water content of the first distillate (10 kg) during the distillation was not larger than 10 ppm by weight.

It is seen from this result that distillation of HFC-32 which contains water easily removes water.

Example 3

Using the same distillation column as in Example 2, a mixture of HFC-32, HCFC-31 and HCC-30 which contains water at 400 ppm by weight was supplied to the column at a flow rate of about 40 kg/hr at the twentieth plate from the top of the column. Operating the distillation at a reflux ratio of 5 and an operation pressure of 20 kg/cm$^2$-abs. (a top temperature was 30° C.), and a portion (about 20 kg/hr) of the reflux liquid stream was distilled off as a distillate.

Water contents and concentrations of the other components of the supplied mixture, the distillate and the bottom product of the distillation are shown in Table 2.

TABLE 2

|  | Water (wt ppm) | HFC-32 (mol %) | HCFC-31 (mol %) | HCC-30 (mol %) |
| --- | --- | --- | --- | --- |
| Supplied mixture | 400 | 68.8 | 29.2 | 1.9 |
| Distillate | ≦10 | 100 | N/D | N/D |
| Bottom Product | 720 | 37.8 | 58.4 | 3.8 |

N/D: not detected

It is seen from the results of Table 2 that even in the case wherein HCFC-31 and HCC-30 as additional components are contained in addition to HFC-32, the water removal is possible. Further, these additional components are simultaneously separated and removed so that HFC-32 is obtained having a higher purity.

What is claimed is:

1. A process for producing difluoromethane which comprises subjecting a feed mixture comprising water and difluoromethane to distillation to distill off a second mixture for removal comprising difluoromethane with a reduced water content of not larger than 50% of the original water content in the feed mixture.

2. The process according to claim 1, wherein the feed mixture further comprises chlorofluoromethane and/or dichloromethane.

3. The process according to claim 1, wherein the feed mixture is a reaction effluent from a reaction step which produces difluoromethane, and a bottom product obtained by the distillation is recycled to the reaction step which produces difluoromethane.

4. The process according to claim 3, wherein an antimony catalyst is used in the reaction step.

5. The process according to claim 1, wherein the second mixture has a water content of not larger than 5% of the feed mixture.

6. The process according to claim 1, wherein the distillation step is conducted under a pressure in the range of 10 to 40 kg/cm$^2$-abs. and in a temperature range of 5 to 60° C.

7. The process according to claim 1, wherein the distillation step is conducted under a pressure in the range of 15 to 35 kg/cm$^2$-abs. and in a temperature range of 20 to 55° C.

8. The process according to claim 1, wherein the distillation step is conducted under a pressure in the range of 20 to 30 kg/cm$^2$-abs. and in a temperature range of 30 to 50° C.

* * * * *